United States Patent

Kanesaka

[11] Patent Number: 5,514,158
[45] Date of Patent: May 7, 1996

[54] SEALING DEVICE FOR A PERCUTANEOUS PUNCTURE

[76] Inventor: Nozomu Kanesaka, 36 Cathy Rd., Hillsdale, N.J. 07642

[21] Appl. No.: 17,702

[22] Filed: Dec. 28, 1992

[51] Int. Cl.$^6$ ................................................ A61B 17/04
[52] U.S. Cl. ............................................ 606/213; 604/11
[58] Field of Search ............................. 606/151, 214, 606/213; 604/11, 13; 602/42–48

[56] References Cited

U.S. PATENT DOCUMENTS

| | | | |
|---|---|---|---|
| 636,637 | 11/1899 | Cooke | 604/13 |
| 5,176,692 | 1/1993 | Wilk et al. | 606/151 |
| 5,304,187 | 4/1994 | Green et al. | 606/151 |
| 5,334,216 | 8/1994 | Vidal et al. | 606/151 |
| 5,350,387 | 9/1994 | Semm | 606/151 |

*Primary Examiner*—Gary Jackson
*Attorney, Agent, or Firm*—Kanesaka & Takeuchi

[57] ABSTRACT

A device of the invention is used for preventing bleeding through a puncture of a body. The device includes an elongated member, a hemostatic material situated around the elongated member, and a cover member for completely covering the hemostatic material. The cover member includes an inner edge fixed to the elongated member. After the device is inserted into the puncture, the elongated member and the cover are removed from the puncture to leave the hemostatic material in the puncture. The hemostatic material prevents bleeding through the puncture.

9 Claims, 4 Drawing Sheets

SEALING DEVICE FOR A PERCUTANEOUS PUNCTURE

BACKGROUND OF THE INVENTION AND RELATED ART STATEMENT

The present invention relates to a sealing device for a percutaneous puncture, in particular to an applicator device to seal a percutaneous puncture in a body or blood vessel of a patient.

Various intravascular and intralumenal surgical operations are routinely performed on a patient through catheterization by opening a puncture in the patient. Typical operations are cardiac output measurements with Swanguns catheter by thermal dilution method; cardiac, neurological, and vascular angiography; percutaneous transluminal coronary angioplasty(PTCA); and peripheral transluminal angioplasty(PTA). In all of those operations, a patient's arterial vessel is punctured by a needle, and various types of guide wires and catheters are inserted into the vessel through a puncture. After the procedure, the catheter is withdrawn and the puncture site is mechanically clamped or pressurized for several hours, typically up to 12 hours to prevent bleeding. Under these operations, most patients are heparinized, i.e. coagulation of blood is lessened, so that bleeding does not stop easily.

One method being attempted to shorten the bleeding is to insert a pellet of collagen into the puncture site through a sheath. In this method, firstly, the depth of the artery from the skin is measured by a needle when the puncture is made by the needle. Then, a device with a predetermined length, which is formed of a sheath and a dilator or a rounded stick slidably situated in the sheath, is selected. Thereafter, the device is inserted in the puncture. Now, the dilator is removed from the sheath, and collagen pellet is inserted into the sheath and is pushed forwardly inside the sheath by a plunger. Once the plunger goes all the way to the forward end of the sheath, the plunger is held and the sheath is taken out slowly. Collagen stays in the puncture site. If necessary, another pellet may be further applied to fully fill out the puncture.

Collagen is a fibrous material, and once blood is absorbed by collagen, the collagen starts to activate platelets to form coagulum. Thus, the puncture is blocked and bleeding is effectively stopped.

In the applicator as stated above, the whole system is formed of the sheath, the plunder, one or more collagen pellet, and a dilator. Also, there are many steps to perform and the process is very complicated. Namely, the collagen pellets must be pushed by the plunger and the sheath must be withdrawn slowly. Moreover, it is very difficult to control the depth of collagen being placed, because the placement of the collagen pellets is very critical, i.e. collagen should not go into the artery.

Accordingly, one object of the invention is to provide a simplified applicator device to apply a strip of hemostatic material directly in the percutaneous puncture site to prevent bleeding without using a complicated devices.

Another object of the invention is to provide an applicator device as stated above, wherein the applicator device can be inserted into the puncture site and release hemostatic material at the exact depth without learning a special skill.

Further objects and advantages of the invention will be apparent from the following description of the invention.

SUMMARY OF THE INVENTION

In accordance with the present invention, bleeding through a puncture of a body is easily prevented. The device is formed of an elongated member, a hemostatic material situated around the elongated member, and a cover member for completely covering the hemostatic material. The cover member includes inner and outer edges. The inner edge is fixed to the elongated member, and the outer edge is situated over a part of the cover member to completely cover the hemostatic material.

In case the present device is used, depth of a needle from a skin to an artery must be noted when the catheterization begins by puncturing with the needle. After the catheterization procedure is over, the device is inserted into the puncture hole to the same depth as noted at the beginning of the catheterization.

After the device is inserted into the puncture to the exact depth as noted above, the elongated member is rotated to wind the cover member completely over the elongated member, thus exposing the hemostatic material. Then, the elongated member with the cover is removed from the puncture to leave the hemostatic material in the puncture. Thus, bleeding through the puncture is easily and effectively prevented.

The outer edge of the cover member may be sewed to the part of the cover by means of a filament. In this case, the filament is removed before the cover is rolled up over the elongated member. Also, a rotating knob may be attached at the proximal end of the elongated member to easily wind the cover.

The elongated member may be a solid form or may includes a hole like a tube. A guide wire may pass through the hole of the elongated member so that the device may be located in the puncture by means of the guide wire.

When the device or applicator is supplied, a strip of hemostatic material is already placed inside the cover and wound onto the elongated member with the cover exposed to the outside to form a cylindrical shape. The device is formed to have a round end, so that the device can be easily inserted into the puncture.

DETAILED DESCRIPTION OF PREFERRED EMBODIMENTS

A percutaneous puncture of a vessel is a common surgical procedure for catheterization. After surgical operation, however, a puncture hole must be closed. In order to avoid prolonged bleeding after the surgical operation, generally, the puncture site is pressurized or a hemostatic material is applied. In the invention, the hemostatic material can be filled in the puncture hole easily to stop bleeding.

Figure 1:
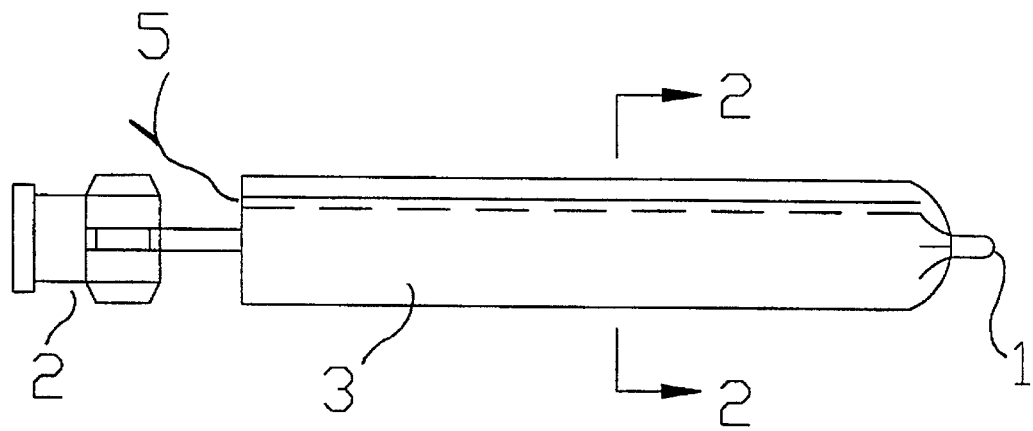
FIG. 1 is a side view of the sealing device for a percutaneous puncture.

As shown in FIG. 1, the invention includes an elongated member 1, a knob 2 firmly attached to the proximal end of the elongated member 1, a cover member 3 made of a flexible material like plastic, and a hemostatic material 4 such as collagen. The hemostatic material 4 is covered by the cover member 3 and is wound over the elongated member 1.

Figure 3:
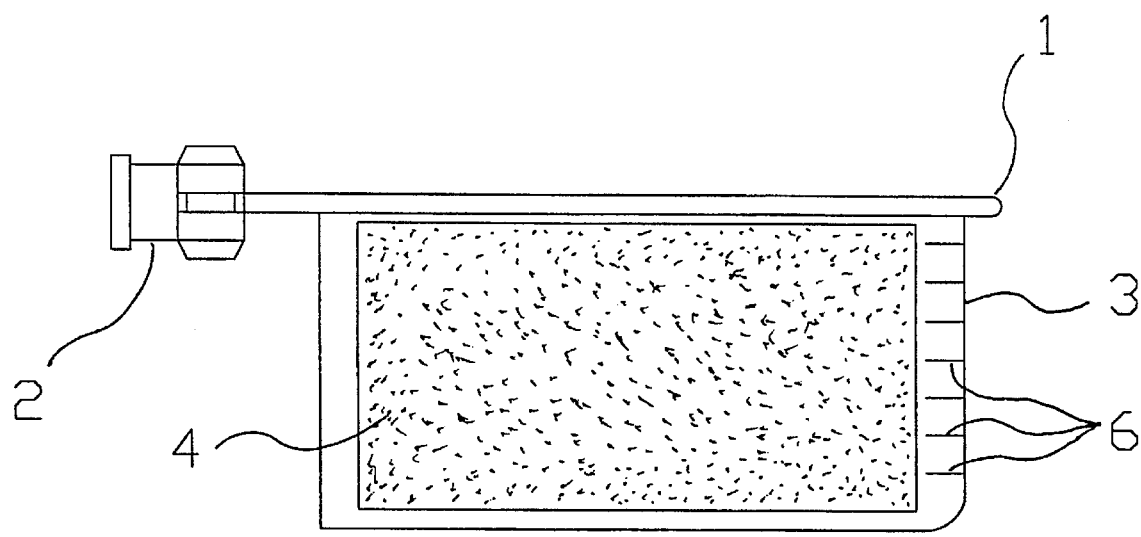
FIG. 3 is a side view of the applicator in an unwound position for showing a full view of the elongated member and hemostatic material.

A filament 5 is stitched to the outer layer of the cover member 3 for holding the outer edge of the cover member 3 in a sealed position. As shown in FIG. 3, the cover member 3 includes serrations 6 at a front end, and is fixed to the elongated member to have a round edge.

Figure 2:
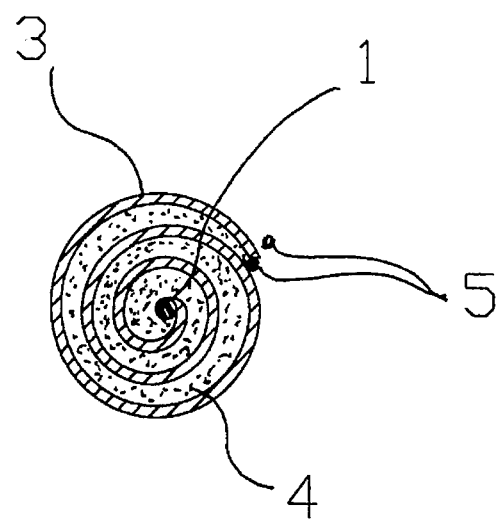
FIG. 2 shows a cross section taken along a line 2—2 of FIG. 1 of the sealing device for a percutaneous puncture.

When the sealing device is prepared, the cover member 3 is opened, and the hemostatic material 4 is disposed over the cover member 3. Then, the elongated member 1 is wound to roll up the cover member 3 and the hemostatic material 4. The front end of the cover member 3 is formed to have a round end. Then, the filament 5 is sewed to a part of the cover member 3, as shown in FIGS. 1 and 2.

In a common surgical catheterization, a percutaneous puncture is made by a needle to the desired site and the depth of the needle to the vessel from the skin surface is noted. After the catheterization or the procedure is completed, the sealing device of the invention is applied to close the puncture hole.

If a guide wire is left at the puncture site or reinserted before the withdrawal of the catheter, the sealing device or an applicator can utilize the guide wire for directing the applicator into the proper puncture site and to the depth as noted above.

In this procedure, the proximal end of the guide wire exposed from the patient is used to thread into the distal end of the hollow elongated member 1 and to exit from the knob 2. The hollow elongated member 1 advances down along the guide wire into the puncture site or hole.

Figure 7:
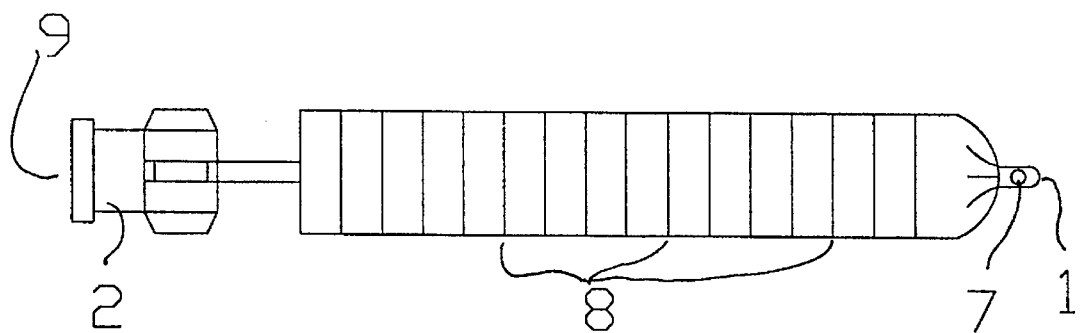
FIG. 7 shows a side view of the applicator with sign marks to measure the depth of insertion from the tip.

The sealing device is inserted into the premeasured depth with reference to the sign markers 8 as shown in FIG. 7. If the hollow elongated member 1 reaches the inside of a vessel, blood comes out from the end of the knob 2 to indicate that the distal end of the needle is in the vessel. The sealing device is then pulled back slightly until the blood flow stops and the hemostatic material 4 is released at the site.

Figure 4:
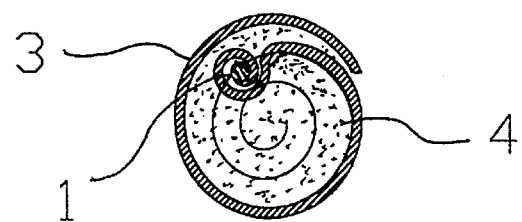
FIG. 4 shows a cross section view, similar to FIG. 2, wherein the cover member is partially wrapped onto the elongated member.
Figure 5:
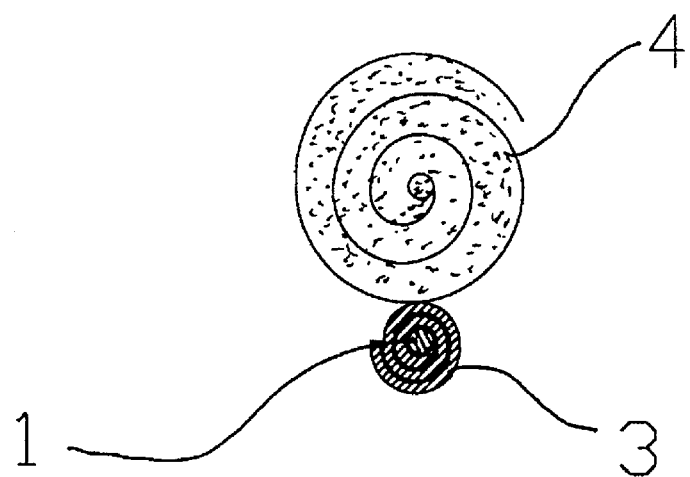
FIG. 5 shows a cross section view, similar to FIG. 2, wherein the cover member is completely wound onto the elongated member and ready for extraction.

Namely, after the sealing device is inserted into the proper depth, the filament 5 is pulled out to disengage the outer edge of the cover member 3. Then, the elongated member 1 is rotated in the clockwise direction by using the knob 2 to unwind the cover member 3 as shown partially in FIG. 4. The elongated member 1 is further rotated in the same direction to wind the cover member 3 directly on the elongated member 1 without the hemostatic material 4. The elongated member 1 and the cover member 3 are then taken out from the puncture hole. Thus, the hemostatic material 4 is left and exposed in the puncture hole. The hemostatic material 4 absorbs blood and closes the puncture hole.

Figure 6:
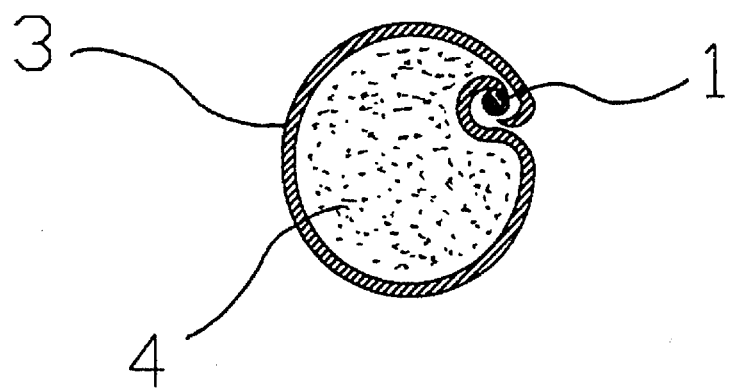
FIG. 6 shows a cross section view of another sealing device, with a different way of wrapping the hemostatic material.

FIG. 6 shows an alternative option of winding the hemostatic material around the elongated member 1 in the offset position. In this configuration, the outer edge of the cover member 1 is rolled into the elongated member 1 together with the inner edge of the same cover member 1 such that the two surfaces of the cover member 1 are in direct contact to seal the hemostatic material 4.

Also, as shown in FIG. 7, the sealing device may have a side opening 7, i.e. one or more opening. The side opening 7 communicates with the end opening 9 through the hole of the elongated member 1 and the knob 2. When the sealing device is inserted in the puncture hole, the side opening 7 is sealed by the side wall of the body, so that blood does not enter into the side opening 7. However, once the side opening 7 reaches the vessel, blood will flow through the side opening 7 and is seen through the end opening 9. The sealing device is pulled back slightly until the blood flow stops and the hemostatic material 4 is released. The side opening 7 can indicate the proper position of the sealing device in the puncture hole.

In the invention, the hemostatic material 4 is easily applied to the puncture hole and stops bleeding of a patient.

The description of the present invention contained herein is directed to a percutaneous puncture in the vessel, but the applicator can be utilized for insertion of various other materials into holes of not only living bodies but into any other matters with precise control of depth.

While the invention has been explained with reference to the specific embodiments, the invention is limited only by the appended claims.

What is claimed is:

1. A device for preventing bleeding through a puncture of a body, comprising:

an elongated member, a cover member having an inner edge fixed to the elongated member, and a hemostatic material removably fixed to and completely covered by the cover member so that after the device is inserted into the puncture, the elongated member and the cover are removed from the puncture to leave the hemostatic material in the puncture for preventing bleeding through the puncture.

2. A device according to claim 1, wherein said cover member includes an outer edge, said outer edge being fixed to a part of the cover member in order to keep the device in a wound position.

3. A device according to claim 2, wherein said outer edge is sewed to the part of the cover member by a filament, said filament being taken out before the elongated member and the cover member are removed.

4. A device according to claim 1, wherein said hemostatic material and the cover member are wound over the elongated member, said cover being completely wound over the elongated member before the elongated member is removed from the puncture so that the hemostatic material is left in the puncture.

5. A device according to claim 4, wherein said elongated member is located in a center of the device.

6. A device according to claim 1, wherein said elongated member includes a hole to allow a guide wire to pass through the hole of the elongated member so that the device is inserted into the puncture along the guide wire.

7. A device according to claim 6, wherein said elongated member includes a knob at one end thereof to facilitate rotation of the elongated member.

8. A device according to claim 7, wherein said elongated member is sealed at a distal and having a side opening at the distal end distal to communicate with a proximal end of the elongated member so that blood can flow to the knob when the side opening is in a blood vessel.

9. A device according to claim 1, wherein said cover member includes signs on an outer surface thereof to indicate distances from a forward end of the device.

\* \* \* \* \*